(12) United States Patent
Gattiker et al.

(10) Patent No.: US 9,999,788 B2
(45) Date of Patent: Jun. 19, 2018

(54) FAST AND ACCURATE PROTON THERAPY DOSE CALCULATIONS

(71) Applicant: International Business Machines Corporation, Armonk, NY (US)

(72) Inventors: Anne E. Gattiker, Austin, TX (US); Damir A. Jamsek, Austin, TX (US); Sani R. Nassif, Austin, TX (US); Thomas H. Osiecki, Austin, TX (US); William E. Speight, Austin, TX (US); Chin Ngai Sze, Austin, TX (US); Min-Yu Tsai, Taipei (TW)

(73) Assignee: International Business Machines Corporation, Armonk, NY (US)

( * ) Notice: Subject to any disclaimer, the term of this patent is extended or adjusted under 35 U.S.C. 154(b) by 614 days.

(21) Appl. No.: 14/596,940

(22) Filed: Jan. 14, 2015

(65) Prior Publication Data

US 2015/0352374 A1   Dec. 10, 2015

Related U.S. Application Data

(60) Provisional application No. 62/008,393, filed on Jun. 5, 2014.

(51) Int. Cl.
*G06F 7/60* (2006.01)
*G06F 17/10* (2006.01)
(Continued)

(52) U.S. Cl.
CPC ......... *A61N 5/1048* (2013.01); *A61N 5/1031* (2013.01); *A61N 2005/1074* (2013.01); *A61N 2005/1087* (2013.01); *G06F 17/50* (2013.01)

(58) Field of Classification Search
None
See application file for complete search history.

(56) References Cited

U.S. PATENT DOCUMENTS

| 6,029,079 | A | * | 2/2000 | Cox | ..................... A61N 5/1031 600/407 |
| 6,148,272 | A | | 11/2000 | Bergstrom et al. | |

(Continued)

OTHER PUBLICATIONS

Conte, V et al., "Track Structure of Light Ions: Experiments and Simulations", Sep. 7, 2012, New Journal of Physics 14, IOP Publishing Ltd.*

(Continued)

*Primary Examiner* — Cedric Johnson
(74) *Attorney, Agent, or Firm* — Tutunjian & Bitetto, P.C.; Mercedes L. Hobson

(57) ABSTRACT

Simulating particle beam interactions includes identifying a set of n functions $F_1, F_2, \ldots, F_n$ corresponding to a plurality of different physical aspects of a particle beam, performing simulations of each $F_i$ using a full physics model, selecting for each $F_i$ a distribution function $f_i$ that models relevant behavior and reducing computation of the full physics model for each $F_i$ by replacing $F_i$ with a distribution function $f_i$. The computation reduction includes comparing a set of simulations wherein each $f_i$ replaces its respective $F_i$ to determine if relevant behavior is accurately modeled and selecting one of $f_i$ or $F_i$ for each n, for a Monte Carlo simulation based on a runtime and accuracy criteria.

25 Claims, 10 Drawing Sheets

Electromagnetic Interactions

Elastic & Inelastic Nuclear Interactions

(51) Int. Cl.
  A61N 5/10     (2006.01)
  G06F 17/50    (2006.01)

(56) References Cited

U.S. PATENT DOCUMENTS

| | | | |
|---|---|---|---|
| 6,714,620 | B2 | 3/2004 | Caflisch et al. |
| 6,792,073 | B2 | 9/2004 | Deasy et al. |
| 8,125,813 | B2 | 2/2012 | Nizin et al. |
| 8,145,459 | B2 | 3/2012 | Holland |
| 2006/0145088 | A1* | 7/2006 | Ma .................... G21K 1/08 250/396 ML |
| 2006/0285640 | A1* | 12/2006 | Nizin .................. A61N 5/1031 378/65 |
| 2008/0128626 | A1* | 6/2008 | Rousso ................. A61B 5/418 250/362 |
| 2009/0110145 | A1* | 4/2009 | Lu ...................... A61N 5/103 378/65 |
| 2012/0136194 | A1* | 5/2012 | Zhang ................. A61N 5/103 600/1 |
| 2014/0032185 | A1 | 1/2014 | Yepes et al. |

OTHER PUBLICATIONS

Waters, L., "MCNPX user's manual version 2.4.0, Los Alamos National Laboratory Report LA-CP-02-408" (Sep. 2002) pp. 1-427.

Hotta, K. et al., "Improved dose-calculation accuracy in proton treatment planning using a simplified Monte Carlo method verified with three-dimensional measurements in an anthropomorphic phantom" Phys. Med. Biol. (2010) pp. 3545-3556, vol. 55.

Yepes, P. et al., "A GPU implementation of a track-repeating algorithm for proton radiotherapy dose calculations" Phys Med Biol. (Dec. 2010) pp. 7107-7120, vol. 55.

Pagnetti, H. et al., "Clinical implementation of full Monte Carlo dose calculation in proton beam therapy" Phys. Med. Biol. (2008) pp. 4825-4853, vol. 53.

Depauw, N., "A path towards adaptive proton pencil beam scanning therapy" University of Wollongong Thesis (2014) pp. 1-191.

Jia, X. et al., "GPU-based fast Monte Carlo dose calculation for proton therapy" Phys. Med. Biol. (2012) pp. 7783-7798, vol. 57.

Fippel, M. et al., "A Monte Carlo dose calculation algorithm for proton therapy" Med Phys. (Aug. 2004) pp. 2263-2273, vol. 31, No. 8.

Perl, J. et al., "TOPAS—An innovative proton Monte Carlo platform for research and clinical applications" Medical Physics (Nov. 2012) pp. 6818-6837, vol. 39, No. 11.

Akagi T. et al., "The PTSim and TOPAS Projects, Bringing Geant4 to the Particle Therapy Clinic" Progress in Nuclear Science and Technology (2011) pp. 912-917, vol. 2.

Ferrari, A. et al., "FLUKA: A multi-particle transport code" CERN Yellow Report No. CERN Oct. 2005; INFN/TC 05/11, SLAC-R-773 (CERN, Geneva, 2005) pp. 1-406.

Ma, C. et al., "Implementation of Monte Carlo Dose Calculation for CyberKnife treatment planning" Journal of Physics: Conference Series 102 (2008) pp. 1-10.

Siebers, J. et al., "Monte Carlo Applications in IMRT Planning and Quality Assurance" Med. Phys. (2007) pp. 1-13, vol. 34.

Keall, P.J. et al., "Monte Carlo dose calculations for dynamic IMRT treatments" Phys Med Biol (2001) pp. 929-941, vol. 46, No. 4.

Siebers, J. et al., "A method for photon beam Monte Carlo multileaf collimator particle transport" Phys Med Biol (2002) pp. 3225-3249, vol. 47, No. 17.

Jiang, H. et al., "Adaptation of GEANT4 to Monte Carlo dose calculations based on CT data" Med Phys. (Oct. 2004) pp. 2811-2818, vol. 31, No. 10.

Ilic, R. et al., "SRNA—Monte Carlo Codes for Proton Transport Simulation in Combined and Voxelized Geometries" Nuclear Technology and Radiation Protection (Dec. 2001) pp. 27-36, vol. 17, No. 1-2.

Prinja, A., "Reduced-Order Physics Models for Computationally Efficient Charged Particle Transport" University of New Mexico, workshop on Monte Carlo for Particle Therapy and treatment Planning (May 2011) pp. 1-41.

Fix, M. et al., "Macro Monte Carlo for dose calculation of proton beams" Phys. Med. Biol. (2013) pp. 2027-2044, vol. 58.

Agostinelli et al., "GEANT4—a simulation toolkit," Nuclear Instruments and Methods in Physics Research Section A, vol. 506, No. 3, Dec. 2003. (86 pages).

Allison et al., "Geant4 Developments and Applications," IEEE Transactions on Nuclear Science, vol. 53, No. 1, Feb. 2006, pp. 270-278.

Osiecki et al., "Hardware acceleration of an efficient and accurate proton therapy Monte Carlo," Procedia Computer Science, vol. 18, Jun. 2013, pp. 2241-2250.

Tsai et al., "Hardware Acceleration for Proton Beam Monte Carlo Simulation," Proceedings of the 2013 Research in Adaptive and Convergent Systems, ACM, Oct. 2013, pp. 495-496.

Yepes et al., "Monte Carlo fast dose calculator for proton radiotherapy: application to a voxelized geometry representing a patient with prostate cancer," Physics in Medicine and Biology, vol. 54, No. 1, Jan. 2009, pp. N21-N28.

* cited by examiner

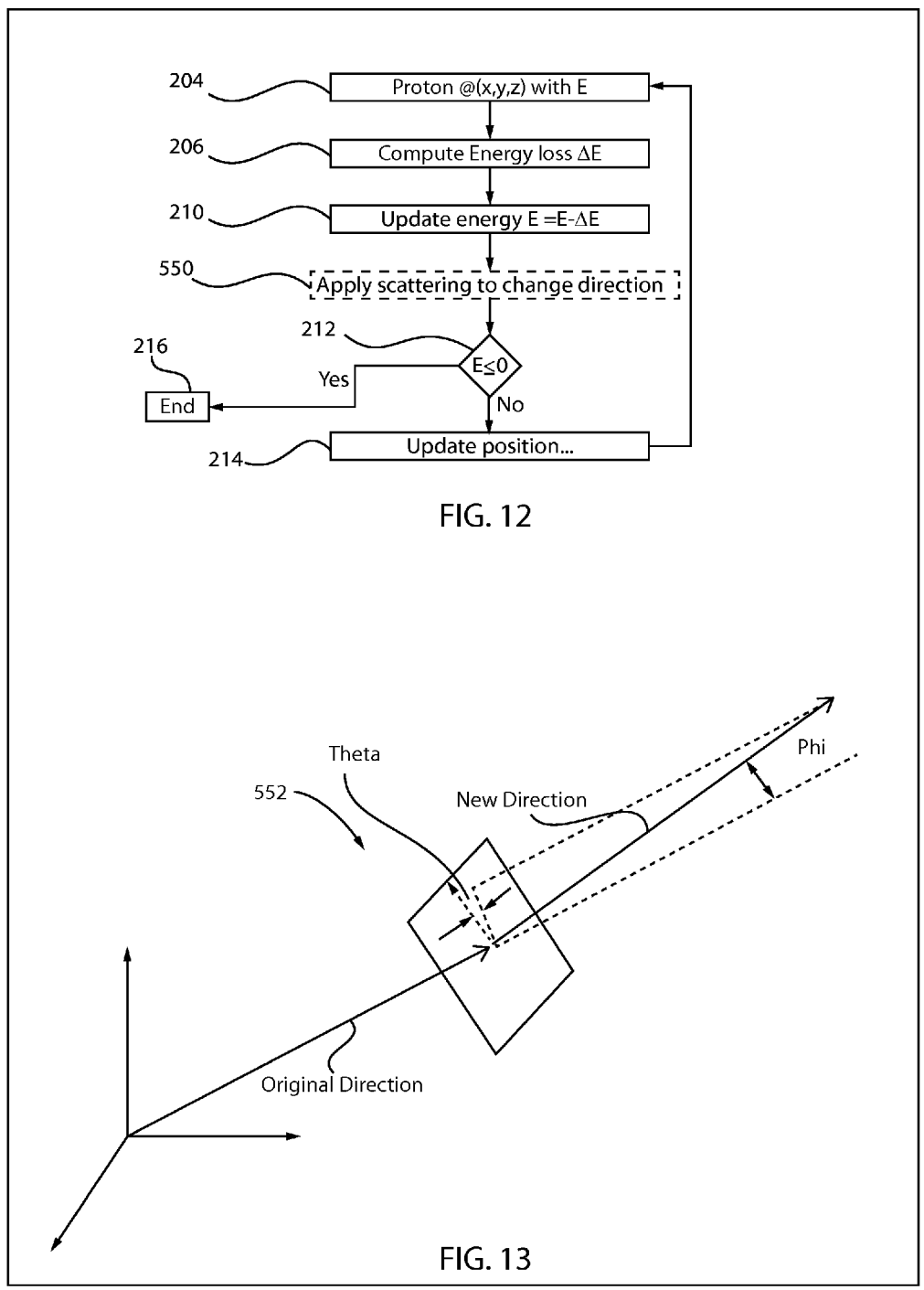

FAST AND ACCURATE PROTON THERAPY DOSE CALCULATIONS

RELATED APPLICATION INFORMATION

This application claims priority to provisional application Ser. No. 62/008,393 filed on Jun. 5, 2014, incorporated herein by reference in its entirety.

BACKGROUND

Technical Field

The present invention relates to radiation therapy, and more particularly to systems and methods for improving computation time for radiation therapy doses.

Description of the Related Art

One effective treatment for cancer utilizes radiation to kill cancer cells. Radiation deposits energy in cells, disrupting DNA thus killing the cell or cells. Cancer therapy using protons is very effective for treatment since proton insertion depth is highly selective. The selective nature of proton radiation makes proton radiation particularly effective in treating cancer. Proton therapy is currently the best form of radiation therapy due to its accuracy and due to its lower long term side effects. Prior to treatment, the radiation dose must be calculated accurately. Unfortunately, modern dose calculators take liberties to permit them to complete computations faster, but with less accuracy.

SUMMARY

A method for simulating particle beam interactions includes identifying a set of n functions $F_1, F_2, \ldots, F_n$ corresponding to a plurality of different physical aspects of a particle beam, performing simulations of each $F_i$ using a full physics model, selecting for each $F_i$ a distribution function $f_i$ that models relevant behavior and reducing computation of the full physics model for each $F_i$ by replacing $F_i$ with a distribution function $f_i$. The computation reduction includes comparing a set of simulations wherein each $f_i$ replaces its respective $F_i$ to determine if relevant behavior is accurately modeled and selecting one of $f_i$ or $F_i$ for each n, for a Monte Carlo simulation based on a runtime and accuracy criteria.

Another method for simulating particle beam interactions includes identifying a set of n functions $F_1, F_2, \ldots, F_n$ corresponding to a plurality of different physical aspects of a particle beam; performing simulations of each $F_i$ using a full physics model; selecting for each $F_i$ a distribution function $f_i$ that models relevant behavior of the particle beam; reducing computation of the full physics model corresponding to each $F_i$ by replacing $F_i$ with the distribution function $f_i$, wherein reducing computation includes: comparing a set of simulations wherein each $f_i$ replaces its respective $F_i$ to determine if relevant behavior is accurately modeled; and selecting one of $f_i$ or $F_i$ for each n, for a Monte Carlo simulation based on a runtime and accuracy criteria.

A system for simulating particle beam interactions includes a dose computation module configured in non-transitory stored media to reduce computation of a full physics model corresponding to a set of n functions $F_1, F_2, \ldots, F_n$ for a plurality of different physical aspects of a particle beam, wherein at least one $F_i$ is replaced with a distribution function $f_i$ to reduce computation, where $f_i$ models relevant behavior of the particle beam. A simulation and optimization module is configured to compare a set of simulations wherein each $f_i$ replaces its respective $F_i$ to determine if relevant behavior is accurately modeled and to select one of $f_i$ or $F_i$ for each n, for a Monte Carlo simulation based on a runtime and accuracy criteria.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 12 is a block/flow diagram showing how to consider angle modeling in a Monte Carlo simulation in accordance with one embodiment;

FIG. 13 is a diagram showing a scattering model defining phi;

DETAILED DESCRIPTION OF PREFERRED EMBODIMENTS

Figure 1:
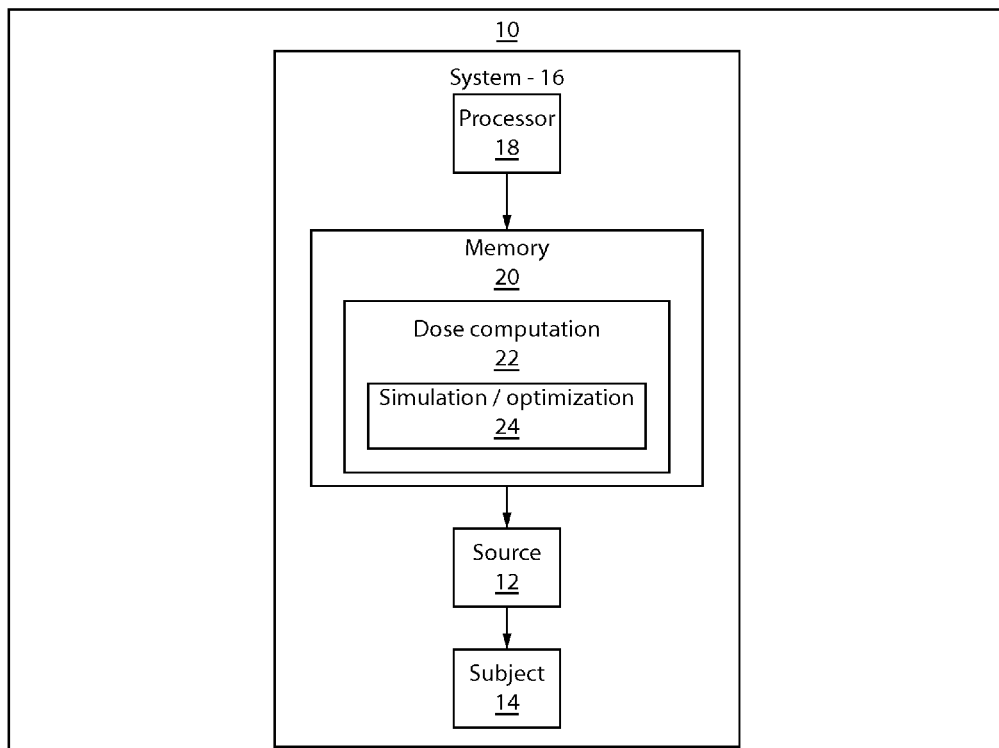
FIG. 1 is a block/flow diagram showing an illustrative radiation therapy system/method in accordance with the present principles.

In accordance with the present principles, systems and methods are provided for a dose calculator for radiation therapy. In particularly useful embodiments, the radiation therapy includes proton therapy. The present principles address the problem of slow dose computation by being faster than and at least as accurate as conventional simulations.

In one embodiment, a method for very fast and highly accurate Monte Carlo simulation for particle beams is employed. Applications for such methods include, e.g., particle therapy for cancer treatment, where examples of particle beams may include proton, neutron, carbon, etc. The methods select a subset of physics models which contribute the most to the accuracy of the simulation results. In particularly useful embodiments, the methods employ probability density functions (pdf) and/or cumulative distribution functions (cdf) to simplify and speed up the computation of multiple physics models.

In addition to the use of selected physics models, hardware acceleration techniques, etc. may also be employed, such as, e.g., multi-core CPU, GPU, FPGA, etc. The method may also include the use of look-up tables to simplify the actual physical equations. In some embodiments, the methods include the use of limited precision (floating point versus double precision computations), the use of fast intrinsic functions (e.g., sin, cos, exp, etc.), the use of fast Random Number Generation, etc.

Existing "accurate" simulations are usually very large and complicated code bases that cover all particles and all physics models associated with them. Proton therapy only needs to be concerned with protons and their associated physics. Hence, a streamlined Monte Carlo simulation is provided for dose computations with further optimization and software techniques for further reducing computation times. Instead of running a complicated physics model each time, a pdf or cdf of the results may be employed as a substitute to provide faster runtimes. The models themselves do not need to be modified so there is no sacrifice to accuracy.

The present principles may include a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the later scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that the present invention will be described in terms of a given illustrative architecture; however, other architectures, structures, materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a system 10 for providing radiation therapy is illustratively shown. The system 10 includes a radiation source 12 for providing and directing radiation dose to a site or subject 14. A computer system 16 includes one or more processors 18 and memory 20. The memory 20 includes a radiation dose computation software module 22 configured to compute the radiation dosage in accordance with a treatment plan or other guideline. A full physics model for simulating a plurality of different physical aspects of a particle beam interaction may be included in the system 10. However, the full physics model may have been run a-priori to develop distributions, wherein the creation of each distribution is carried out via stochastic simulation. The full physics model (F) may include models or simulators that are commercially available, e.g., GEANT™, GEANT4™ or other known models or simulators. Such full physics models may include programs or modules to conduct studies for proton ionization, dE/dx fluctuations, multiple scattering phenomena, Hadronic models including elastic and/or inelastic particle interactions. Other aspects of particle beam generation and interactions may also be simulated using a full physics model. Such models are reduced in accordance with the present principles as herein described.

The radiation dose computation software module 22 may include a simulation and optimization module 24 that is employed to select functions and/or distributions for conducting radiation therapy. The functions/distributions may be selected based on current radiation conditions, aspects of the treatment plan, manual controls, etc. The simulation and optimization module 24 is employed to select functions/distributions that provide the desired radiation energy or dosage in accordance with a physical/physics model, but by employing selected distributions or functions that simulate the output, the desired dose computed by the model is preloaded for rapid deployment.

The simulation and optimization module 24 is configured to reduce computation of the full physics model corresponding to each $F_i$ by replacing $F_i$ with a reduced distribution function, $f_i$, where i is an index. This may be performed by selecting a reduced distribution function that models relevant behavior, wherein the simulation and optimization module compares a set of simulations so that each $f_i$ replaces its respective $F_i$ to determine if relevant behavior is accurately modeled. The simulation and optimization module 24 then selects one of $f_i$ or $F_i$ for each n, for a Monte Carlo simulation based on a runtime and accuracy criteria. The decision to select $f_i$ may be based on other criteria as well. For example, the hardware, software, etc. available for the computations, etc.

The set of n distribution functions may include, e.g., distribution functions that involve one or more of particle energy levels, scattering angles, absorption material and/or particle density. Other possible functions may include magnetic field, ion concentration and other beam generating parameters and/or particle interaction parameters. A person skilled in the art may identify other physical aspects for generating or employing a particle beam.

The particle beam may include protons although other particles may be employed. A particle dosage is preferably computed for a source 12 using at least one $f_i$ to reduce computation time. The dosage may be computed in real-time and be employed to treat a lesion or for other treatment.

It should be understood that FIG. 1 represents an illustrative system and that systems in accordance with the present principles may include other setups and configurations. In useful examples, system 16 may be a planning module for planning a surgical procedure, may include a radiation therapy system, may be a simulation system for testing or training, etc.

Figure 2:
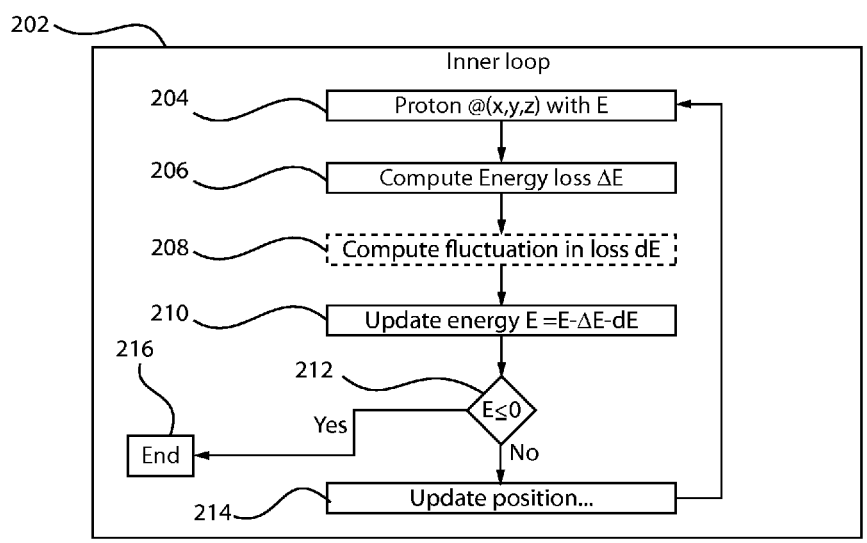
FIG. 2 is a block/flow diagram showing a method for conducting radiation therapy in accordance with the present principles.

Referring to FIG. 2, an example of one model 202 that reduces computation time (e.g., time to run) for updated dosage computations is shown in accordance with the present principles. The model 202 is run, e.g., by the simulation and optimization module 24 (FIG. 1). In block 204, a proton with energy (E) and position (x,y,z) is initialized (e.g., in accordance with a treatment plan). In block 206, an energy loss (ΔE) is computed for the radiation therapy. In block 208, fluctuation in energy loss (dE) is computed. In block 210, energy is updated based on the computed loss and the loss fluctuation. If the energy is less than or equal to zero in block 212, the program ends in block 216. Otherwise, the position of the proton (or beam) is updated for the radiation treatment in block 214 and the program returns to block 204.

The computations of energy loss and energy fluctuations (blocks 206 and 208) are normally computed using larger scale physical models. However, these computations can be optimized by substituting distributions/functions for these (and other) computations to achieve significant time reductions, e.g., 30% or greater. The optimization may include employing software techniques to produce pdf's for fast sampling of the model or to provide pdf's, etc. for quick look-up in a table.

Figure 3:
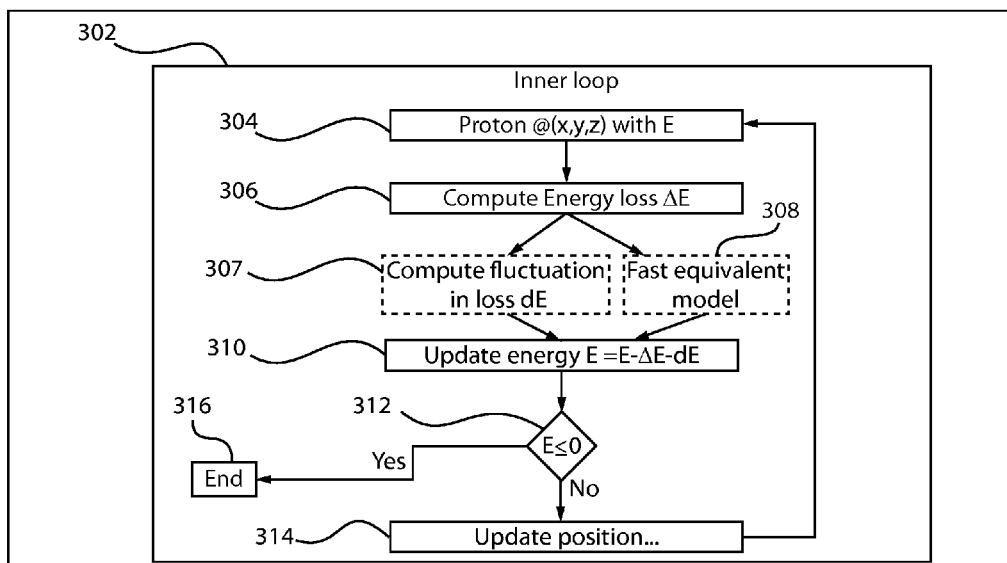
FIG. 3 is a block/flow diagram showing another method for conducting radiation therapy in accordance with the present principles.

Referring to FIG. 3, an example of another model 302 that reduces computation time (e.g., time to run) for updated dosage computations is shown in accordance with the present principles. The model 302 is run, e.g., by the simulation and optimization module 24 (FIG. 1). In block 304, a proton with energy (E) and position (x,y,z) is initialized (e.g., in accordance with a treatment plan). In block 306, an energy loss (ΔE) is computed for the radiation therapy. In block 307, fluctuation in energy loss (dE) is computed for a first model (e.g., a full model). In block 308, a fast equivalent model is provided that simulates a physical model to compute the fluctuation in energy loss and/or the energy loss. In block 310, energy is updated based on the computed loss and the loss fluctuation. If the energy is less than or equal to zero in block 312, the program ends in block 316. Otherwise, the position is updated in block 314 for the radiation treatment, and the program returns to block 304.

The computations of energy loss and energy loss fluctuations (block 306, 307) are normally computed using larger scale physical models. However, these computations can be optimized by substituting distributions/functions for these (and other) computations to achieve significant time reductions, e.g., 30% or greater. The optimization may include employing software techniques to produce pdf's for fast sampling of the model or to provide pdf's, etc. for quick look-up in a table. The systems may include the use of multiple paths (blocks 307 and 308) that compete to compare the result or to use the fastest returned computation. If the models used for the dose computations are all simulated, significant reductions in computation times will make radiation therapy advance rapidly (e.g., full functions versus reduced functions as will be described in greater detail below).

In determining fast equivalent models, the physics of radiation in a subject is considered. Protons slow down because of interactions with electron clouds (frequent, small energy loss), nuclei (rare, large energy loss, new particles generated) in tissues. These interactions are very frequent. Simulators (like GEANT™) use statistical averaging to integrate all interactions over some distance. Predicting such dose distributions can be accurately done via complex and slow Monte Carlo based simulation (using tools such as GEANT™), but such simulators are too slow for use in interactive situations where a doctor is trying to determine the best beams to use for a particular patient.

GEANT™: GEANT™ is a toolkit for the simulation of the passage of particles through matter. Its areas of application include high energy, nuclear and accelerator physics, as well as studies in medical and space science. The GEANT™ series of software toolkits were developed by CERN™, and the first to use object-oriented programming (in C++). Its development, maintenance and user support are undertaken by the GEANT4™ Collaboration. The software is used by a number of research projects around the world.

GEANT4™ includes facilities for handling geometry, tracking, detector response, run management, visualization and user interface. For many physics simulations, this means less time needs to be spent on the low level details, and researchers can start immediately on the more important aspects of the simulation. The scope of GEANT4™ capabilities makes it a very powerful tool, but as this work has shown, it has significant speed drawbacks when it comes to proton therapy. These drawbacks could be mitigated if GEANT4™ could be easily hosted on hardware partly or entirely (e.g., GPU or FPGA), which is not the case.

In accordance with the present principles, an accurate but extremely fast Monte Carlo based proton dose distribution simulator code is employed (e.g., called JACK for ease of reference). The simulator uses the same physics as more complex tools, but leverages massive parallelization and a streamlined code architecture.

The present disclosure focuses on fast Monte Carlo simulations although other fast simulations may be employed. The most accurate physical models have been employed and optimized to eliminate any overhead that they may contain. Throughout the development process, separate code branches were created for other researchers to apply various hardware acceleration techniques.

Physical models most important to proton transport in matter have been considered and employed. Therapy using protons gives certain constraints that permit ignoring physics not relevant to the problem at hand. For example, proton therapy facilities generally use protons with a kinetic energy starting from around 70 to a maximum of 250 MeV/c. At these energies protons undergo electromagnetic and nuclear interactions. Proton electromagnetic interactions involve energy loss via ionization of electrons and multiple Coulomb scattering for directional changes. The energy regime for medical treatment permits higher order energy corrections associated with energy loss calculations to be ignored.

Figure 4:
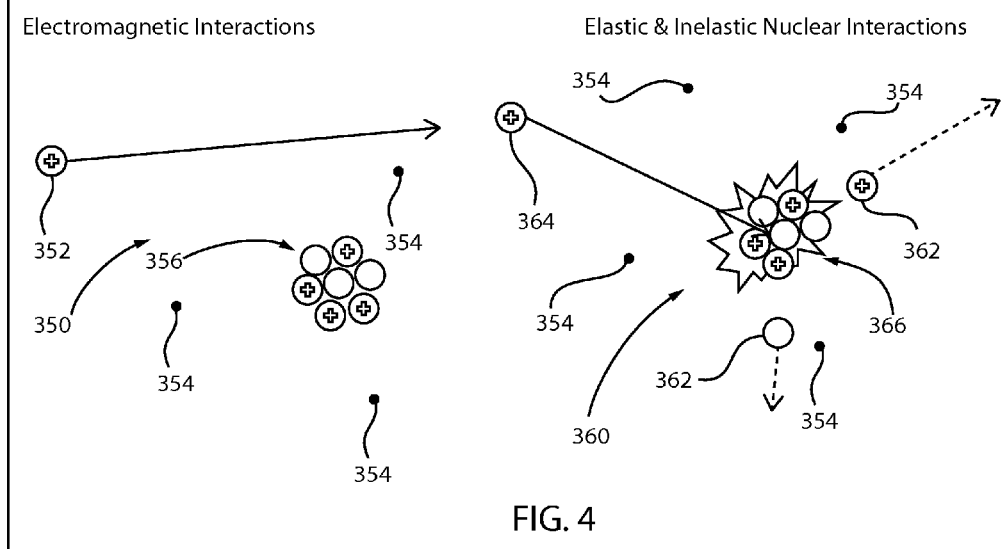
FIG. 4 is a diagram showing proton matter interactions.

Nuclear interactions consist of elastic and inelastic interactions as illustratively depicted in FIG. 4. Inelastic models, in general, contain models for protons up to and above 1 GeV. This, for instance, involves many nuclear resonances that do not need to be modeled under treatment conditions. An interaction 350 shows an electromagnetic interaction where a proton 352 moves through a cloud of electrons 354 surrounding an atomic nucleus 356. An elastic and inelastic nuclear interaction 360 shows a proton 364 impacting an atomic nucleus 366 and recoiling or liberating or protons and/or neutrons 362.

In accordance with illustrative embodiments, models employed in simulations will be further described below. Other models and parameters are also contemplated.

Energy loss through ionization ($\Delta E$): Standard Bethe-Bloch theory is employed along with the most important corrections for density effects, shell corrections, the Barkas-Andersen correction and the higher order Bloch correction. This results in dE/dx values calculated directly from well-established theory. These values are tabulated, and interpolation is employed for energy loss calculations. Liberated electrons travel<<1 mm, which is smaller than all voxel sizes in the geometry employed for treatment scenarios and so their kinetic energy is deposited immediately.

Fluctuations in energy loss (dE): Fluctuations in energy loss can have large impacts on the resulting dosage distribution. For thin layers of material, we can employ the Urban model. For thick absorbers, the straggling function approaches the Gaussian distribution, which is also implemented in the Urban model.

Multiple Coulomb Scattering: Multiple coulomb scattering is implemented partially using Lewis theory and an alternate correction for the tails of the distribution.

Elastic Nuclear Scattering: Protons can elastically scatter off the nuclei within a material. When this occurs, the final states (primary and recoil particles) are derived by sampling from tables of the cumulative distribution function of the center-of-mass scattering angle, and tabulated for a discrete set of kinetic energies. The cdf's are tabulated at 1 degree intervals and sampling is done using interpolation in energy and cdf values. The proton typically scatters off a heavy nucleus. The kinetic energy imparted to the nucleus is therefore treated like the electrons in ionization described above, in that the kinetic energy is deposited immediately due to their extremely short range. Occasionally the incident proton will liberate another proton, which is treated like a new particle and tracked.

Inelastic Nuclear Scattering: In inelastic scattering, the target nucleus is modeled using typical Fermi gas model statistics. The Fermi Energy and Momentum will determine what the distributions of the nucleons position and momentum are in the target nucleus. Once the nucleus is set up, we can compute the impact parameter for the incident proton straight through the nucleus for each nucleon. If the impact parameter is less than a threshold value, related to the interaction cross-section, this signals a collision. After all the initial collisions between the incident and target nucleons are tabulated, we loop over these collisions looking for further collisions and any nuclear captures between nucleons that might occur in addition to propagating all nucleons due to their non-zero momentum. Once there are no more collisions to examine, all nucleons have either left the nucleus, been captured, or remain in the target and are thus untouched. If there is more than one captured nucleon, they are recombined into a heavier particle, typically a deuteron, alpha particle or heavy ion depending on how many particles exist. As with elastic scattering, any secondary heavy ions or particles will have their energy deposited locally. Protons that leave the nucleus are tracked. We focus on validating the inelastic scattering models of JACK and incorporating proper neutron kinematics.

Figure 5:
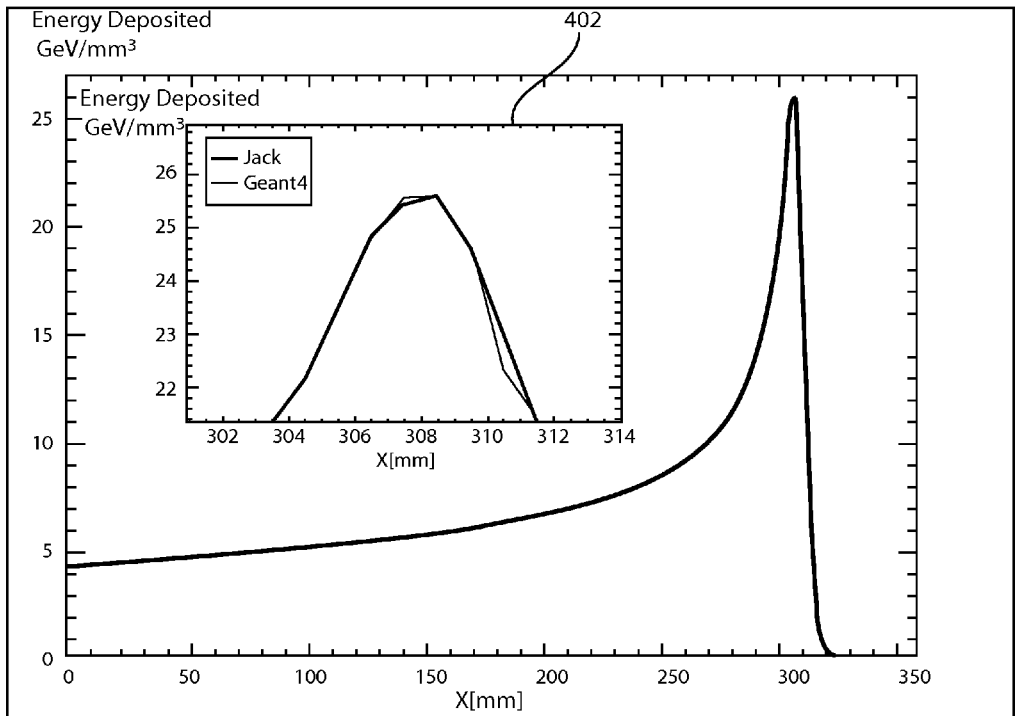
FIG. 5 is a comparison of the present method with GEANT4™.

Monte Carlo and Water Phantom Results: Our initial test for validating JACK was on a simulated water phantom to compare to GEANT4™. The results shown in this section include all electromagnetic effects associated with protons, with nuclear effects to be integrated. FIG. 5 compares energy deposited (GeV/mm$^3$) versus x (mm) between JACK (in accordance with the present principles) and GEANT4™ in the inset 402 and shows a Bragg peak in water for the two techniques. Excellent agreement with GEANT4™ is achieved with no more than a maximum deviation of 2%, and mostly within 1%.

In accordance with the present principles, methods are provided for utilizing Monte Carlo simulations based on a combination of physics models. Probability and Cumulative Distribution Functions are employed to simulate particle beam distribution. This includes creating a set of n probability and cumulative distribution functions by running full physics model simulations on a plurality of different physical aspects comprising energy levels, angles, material, density or other parameters that effect delivery of a particle beam.

The implementation of energy and angle considerations for reducing model complexity and reduction dosage computation time in accordance with the present principles are described hereinafter as examples for reducing dose computations. Next, reduced calculations from the full physical model corresponding to each $F_i$ is performed by transforming $F_i$ to $f_i$ by applying at least one of a probability density function (pdf) and/or a cumulative distribution function (cdf) as described. A set of n simulations are compared wherein each $f_i$ [reduced calculation] replaces a portion of $F_i$ [full simulation]. One of each of the n $f_i$ and $F_i$ are selected for the Monte Carlo simulation based on runtime and accuracy criteria.

The pdfs and/or cdfs are created to replace the full model. The details of how a set of n probability and cumulative distribution functions $f_1, f_2, \ldots, f_n$ are created is described by running full physics model simulations on a plurality of different physical aspects comprising energy levels, angles, material and/or density.

Referring to again FIG. 2, energy loss fluctuation modeling is described in greater detail. The present principles speed up accurate Monte Carlo based proton transport codes for applications in cancer radiation therapy. This is achieved by developing abstract and compact models of proton transport phenomena by determining the type of computations that need to be carried out. In one embodiment, a range of accuracies and computational time tradeoffs are made for one or more phenomena. In this example, energy loss fluctuation is analyzed to illustrate the process.

In block 204, relevant models for a particular phenomenon are extracted from physics models, such as GEANT or GEANT4™. In block 206, the computation of energy loss is performed. Note that each step in the computation is included in a separate module to make it easy to study each computation separately. The energy loss computation is deterministic, and thus a table of $\Delta E$ (energy loss) versus E (energy) may be generated. In block 208, energy loss fluctuation ($\delta E$) is computed. Since energy loss fluctuation is stochastic, a distribution of values may be created by sampling.

Figures 6A, 6B:
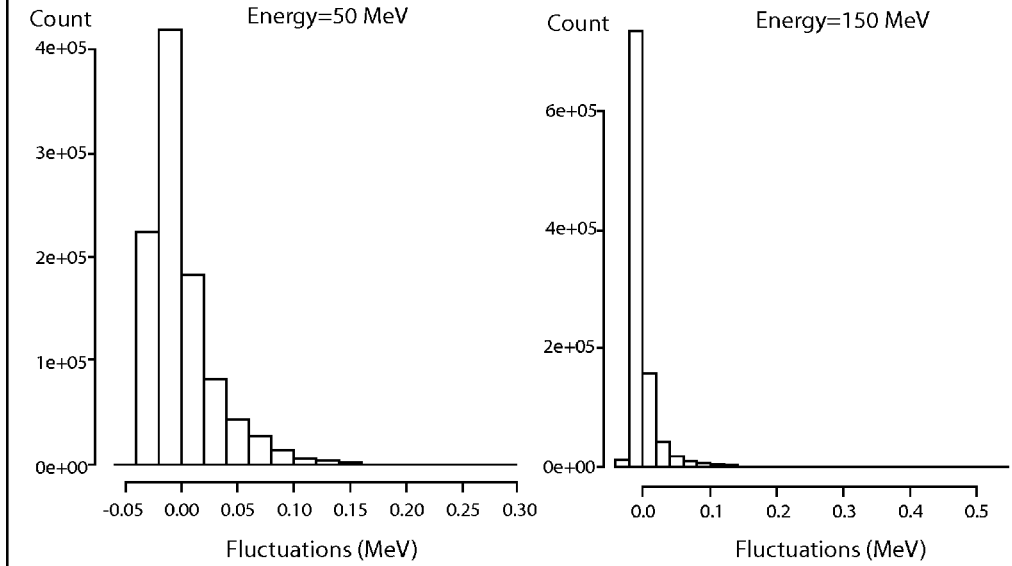
FIG. 6A is a graph showing count versus fluctuations (MeV) for a distribution at an energy of 50 MeV in accordance with one embodiment.
FIG. 6B is a graph showing count versus fluctuations (MeV) for another distribution at an energy of 150 MeV in accordance with one embodiment.
Figures 6C, 6D, 7:
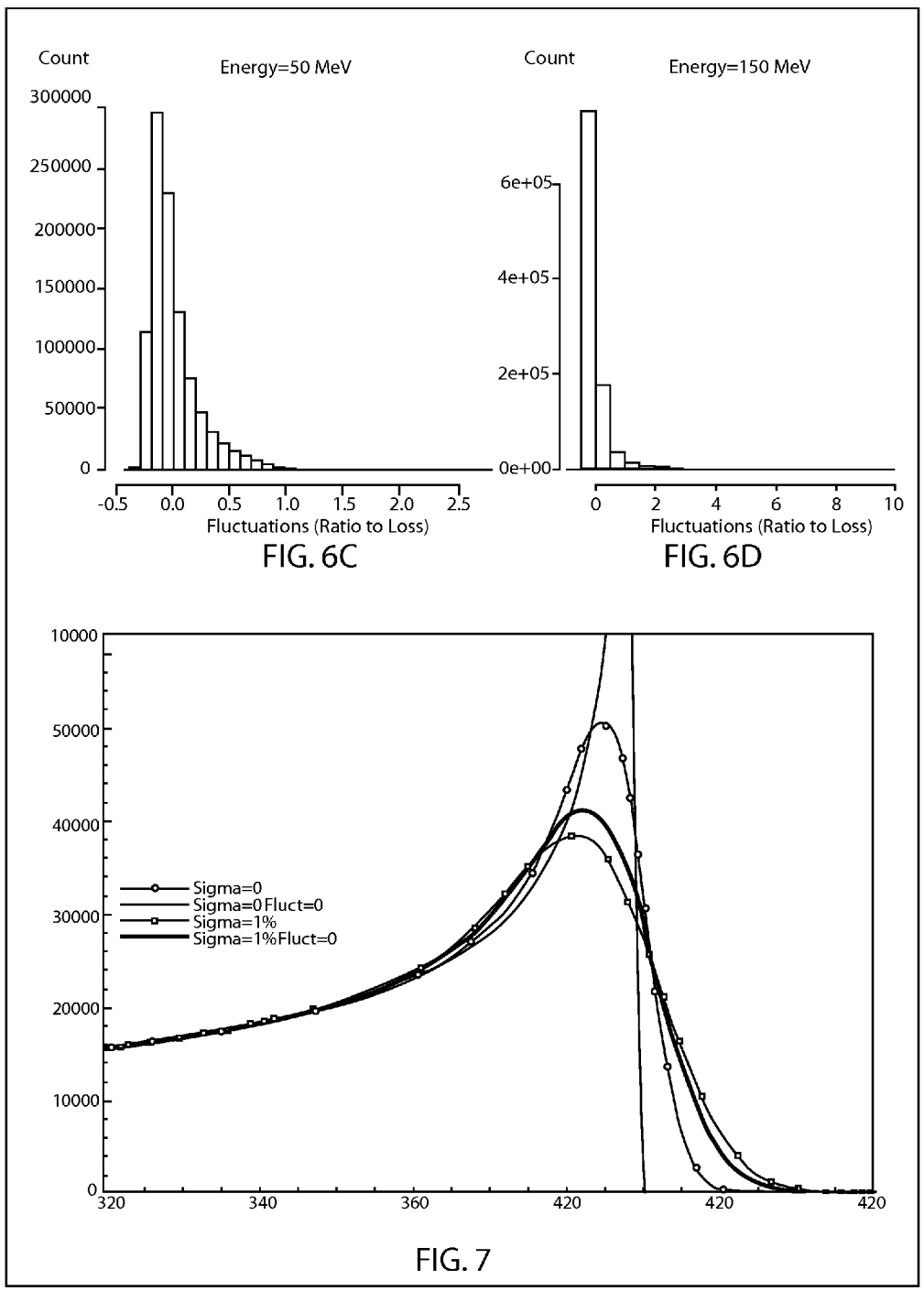
FIG. 6C is a graph showing count versus fluctuations (MeV) (ratio to loss) for another distribution at an energy of 50 MeV in accordance with one embodiment.
FIG. 6D is a graph showing count versus fluctuations (MeV) (ratio to loss) for yet another distribution at an energy of 150 MeV in accordance with one embodiment.
FIG. 7 shows a fluctuation model employed to test changes in a mean for 50,000 protons at energy 100 MeV subjected to the fluctuation model to determine an effect of change in energy in accordance with one embodiment.

Referring to FIGS. 6A-6D, illustrative energy loss fluctuation distributions are shown. FIG. 6A shows a skewed distribution plotting count versus fluctuations (MeV) for an energy E=50 MeV. FIG. 6B shows a long tail high energy distribution plotting count versus fluctuations (MeV) for an energy E=150 MeV. FIG. 6C shows the skewed distribution of FIG. 6A plotting count versus fluctuations (ratio to loss) for an energy E=50 MeV. FIG. 6D shows the long tail high energy distribution of FIG. 6B plotting count versus fluctuations (ratio to loss) for an energy E=150 MeV. The ratio to loss provides information about the absorption of energy from the particle (e.g., proton). Decisions about which parameters can be eliminated can come from such analysis. For example, at the higher energy there is a fairly limited ranged of fluctuations at higher ratios of loss. This permits the elimination of computational complexity where the parameter, distribution, etc. has little impact on the conditions at hand. To be able to make such decisions, distributions for various materials and/or other relevant parameters should be investigated as well as other energy ranges to draw better conclusions about reducing computational complexity.

Referring to FIG. 7, a fluctuation model is employed to test changes in a standard variation (sigma or σ). In this example, 50,000 protons at energy 100 MeV are subjected to the fluctuation model to determine an effect of change in energy. Radiation dosage versus depth in the subject is plotted for sigma=0, sigma=0 and fluctuation=0, sigma=1%, sigma=1% and fluctuation=1%. For σ=0, there are very large differences. For σ=1% there are still significant changes (e.g., approximately 10% change). The magnitude and influence of such changes are considered in evaluating whether portions of the model and/or computations thereof are needed or provide sufficient influences on the result to warrant their consideration in the overall computation. In addition to determining the importance of changes (e.g., in FIG. 7), entire ranges may be eliminated from consideration.

Figure 8:
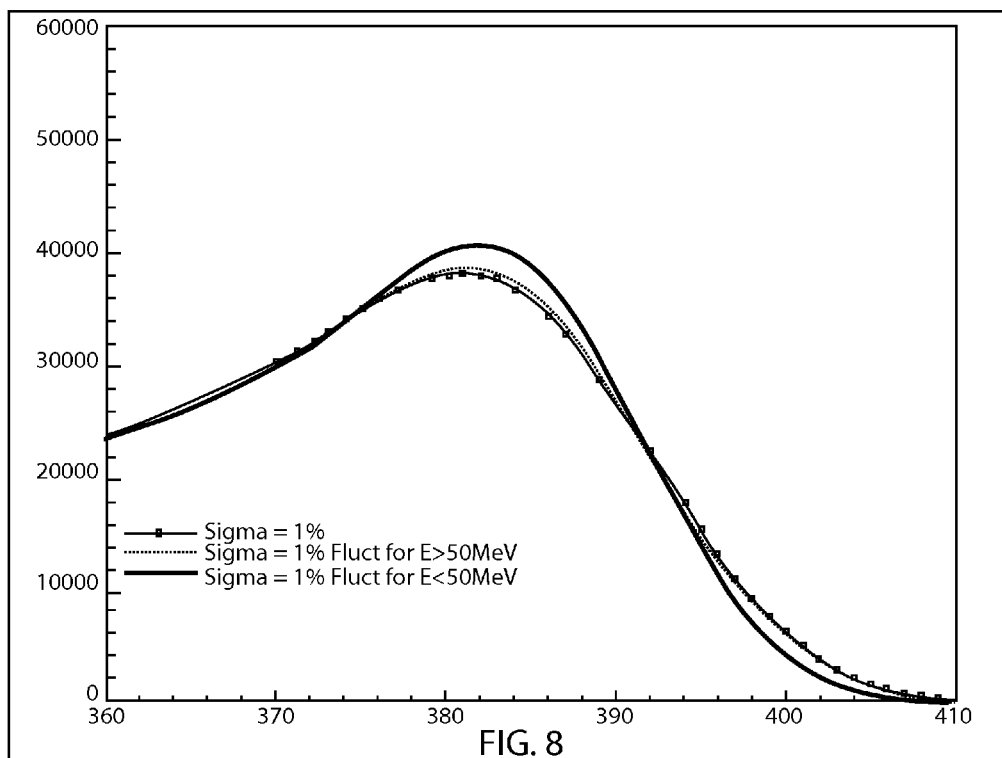
FIG. 8 shows a graph of count versus fluctuations (MeV) plotted for sigma=1% and fluctuations above and below 50 MeV in accordance with one embodiment.

Referring to FIG. 8, radiation dosage versus depth in the subject is plotted for sigma=1% and fluctuations above and below 50 MeV. From the graph, it appears that higher energies are more important or influential than lower energies. With such information, lower energy fluctuations may be eliminated from consideration to reduce the overall computation. An investigation of whether an entire distribution is needed may also be performed.

Figure 9:
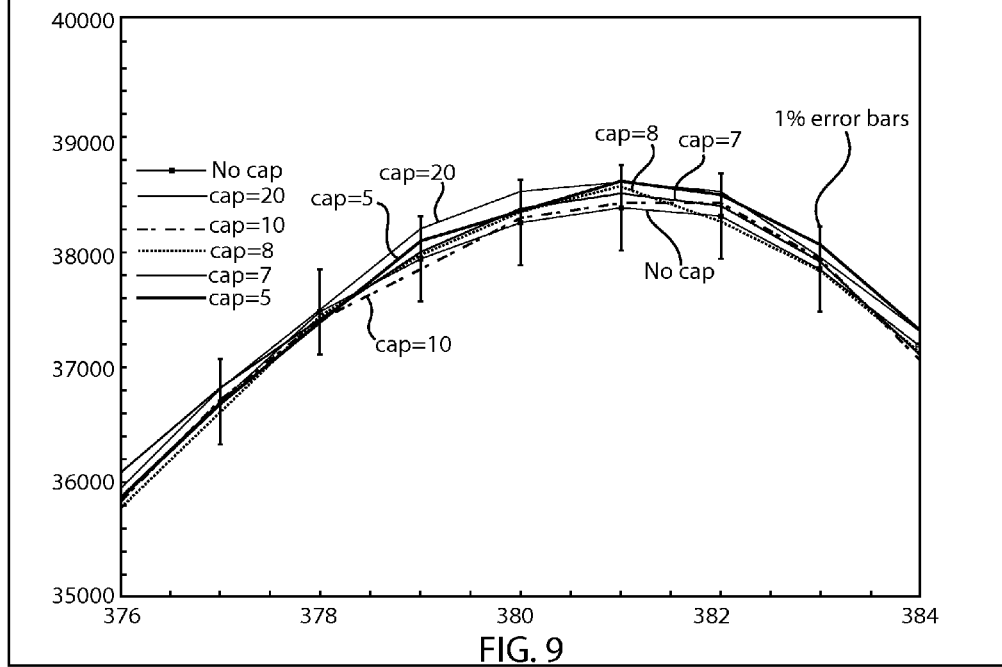
FIG. 9 shows a graph of count versus fluctuations (MeV) plotted for different cap fluctuations in accordance with one embodiment.

Referring to FIG. 9, radiation dosage versus depth in the subject is plotted for different cap fluctuations. A cap of 10 times (cap=10) provides, e.g., fluctuation≤10*loss. As shown a cap=10 works well at approximating a wide range of energies. For distributions with long tails at high energies, not all of the distribution is needed and the distribution can be truncated. By setting limits or caps, simplified data or computations may be substituted for more complicated ones. Here, a cap=10 curve can be substituted over a large range of fluctuation energies with less than 1% error.

Figures 10, 11:
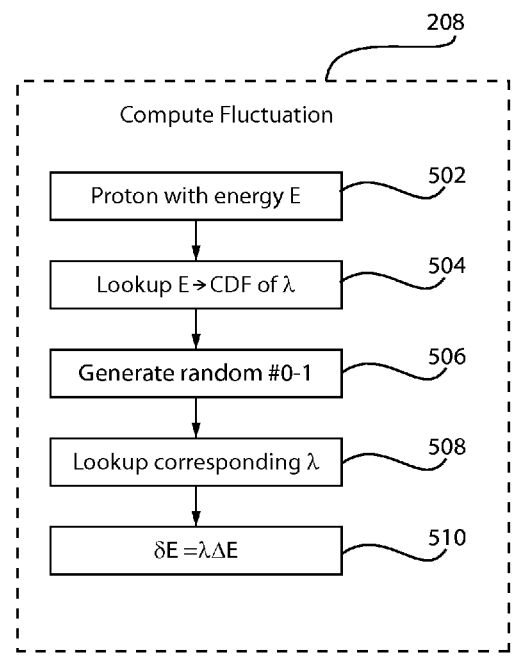
FIG. 10 shows an illustrative look-up table with energy versus loss multipliers in accordance with one embodiment.
FIG. 11 is a block/flow diagram showing an example of how energy loss fluctuation ($\delta E$) is computed in accordance with one embodiment.

Referring to FIG. 10, an illustrative look-up table 400 shows energy 402 versus fluctuation multipliers 404. To avoid interpolation, the energy and multipliers may both be "binned" so that a CDF or PDF 406 can be identified instantly. The accuracy may be provided based on step size where, e.g., a step size of 0.1 for the multiplier and 1 MeV for the energy may be employed. The table size may be, e.g., 100 kB per material. Many materials may be considered. The tables include CDF's and/or PDF's 406 corresponding to loss fluctuation multipliers (probabilities) 404 and energy 402. The values in the table 400 are determined by the prior analysis in determining what influences are relevant and provide sufficient impact on the computation. The values in the table 400 represent reduced probability functions or values that help in reducing the overall computation.

Referring to FIG. 11 with continued reference to FIG. 2, in block 208, energy loss fluctuation (δE) is computed. Since energy loss fluctuation is stochastic, a distribution of values may be created by sampling. A sampling threshold $N_s$ may be set and employed in generating a distribution. In block 502 a proton with energy E is considered. In block 504, lookup E in a lookup table as the first index to determine a CDF of multipliers (λ). In block 506, generate a random number between 0 and 1. In block 508, lookup corresponding multiplier as the second index in the table based upon the random number generated. The random number generator will be employed to generate a plurality of points to be used to generate a distribution. In block 510, energy loss fluctuation is computed based upon the looked up multiplier λ, e.g., δE=λΔE. The results show that the systems and methods in accordance with the present principles provide an accuracy of within 1% error and 21% faster or greater computation time for a water medium at an energy of 50 MeV (25% faster at 200 MeV). These results are illustrative.

Referring to FIG. 12, the flow diagram of FIG. 2 has been modified to consider angle modeling in the Monte Carlo simulation. The angle modeling is another example of a process for creating a more compact model for radiation phenomena. In block 206, the computation of energy loss is performed. In block 210, energy is updated. In block 550, scattering is applied which changes particle direction. For purposes of illustration, electromagnetic scattering is described. Electromagnetic scattering is implemented as a change in the direction of a proton and is a function of energy and material.

Referring to FIG. 13, a diagram shows a scattering model 552. The model includes theta (in-plane) and phi (along the travel direction) to describe a new direction of a scattered particle. Since theta is uniformly distributed, over the range −π to +π, phi is studied.

Figure 14:
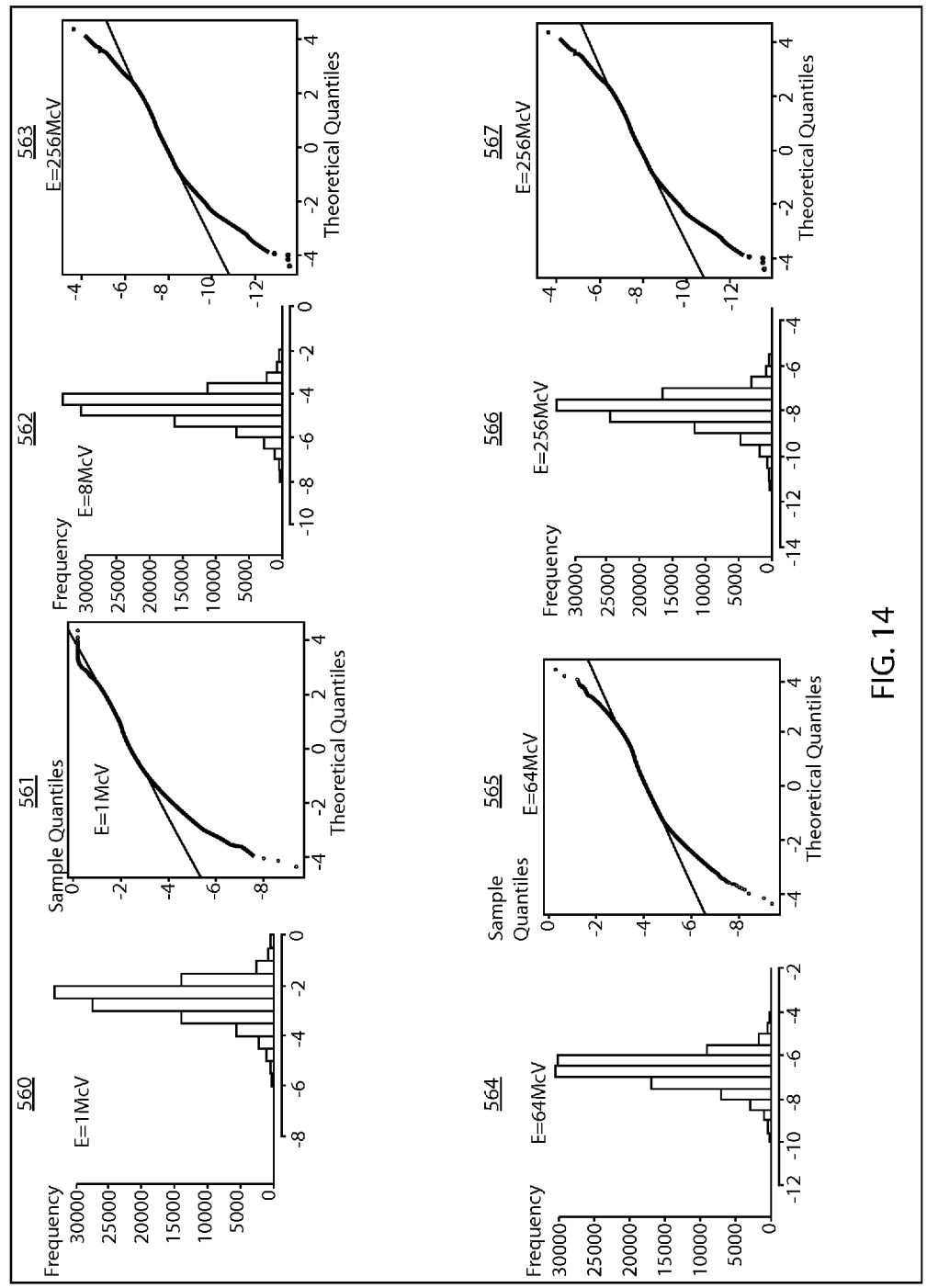
FIG. 14 shows phi distributions versus energy in four sets of distributions with corresponding bar charts and plots for different energies in accordance with one embodiment.

Referring to FIG. 14, phi distributions versus energy are provided. FIG. 14 shows four sets of distributions. Bar charts 560, 562, 564 and 566 plot sampling frequency versus phi (degrees) for energies of 1 Mev, 8 MeV, 64 MeV and 256 MeV, respectively. Plots 561, 563, 565 and 567 graph sample quantiles (y-axis) versus theoretical quantiles (x-axis) for energies of 1 Mev, 8 MeV, 64 MeV and 256 MeV, respectively. The distributions of FIG. 14 are provided to show trends in phi at different energies. At higher energies the distributions are more uniform. This provides higher confidence in predicting outcome and selecting sub-functions or sub-distributions rather than employing whole functions, models or distributions.

Figure 15:
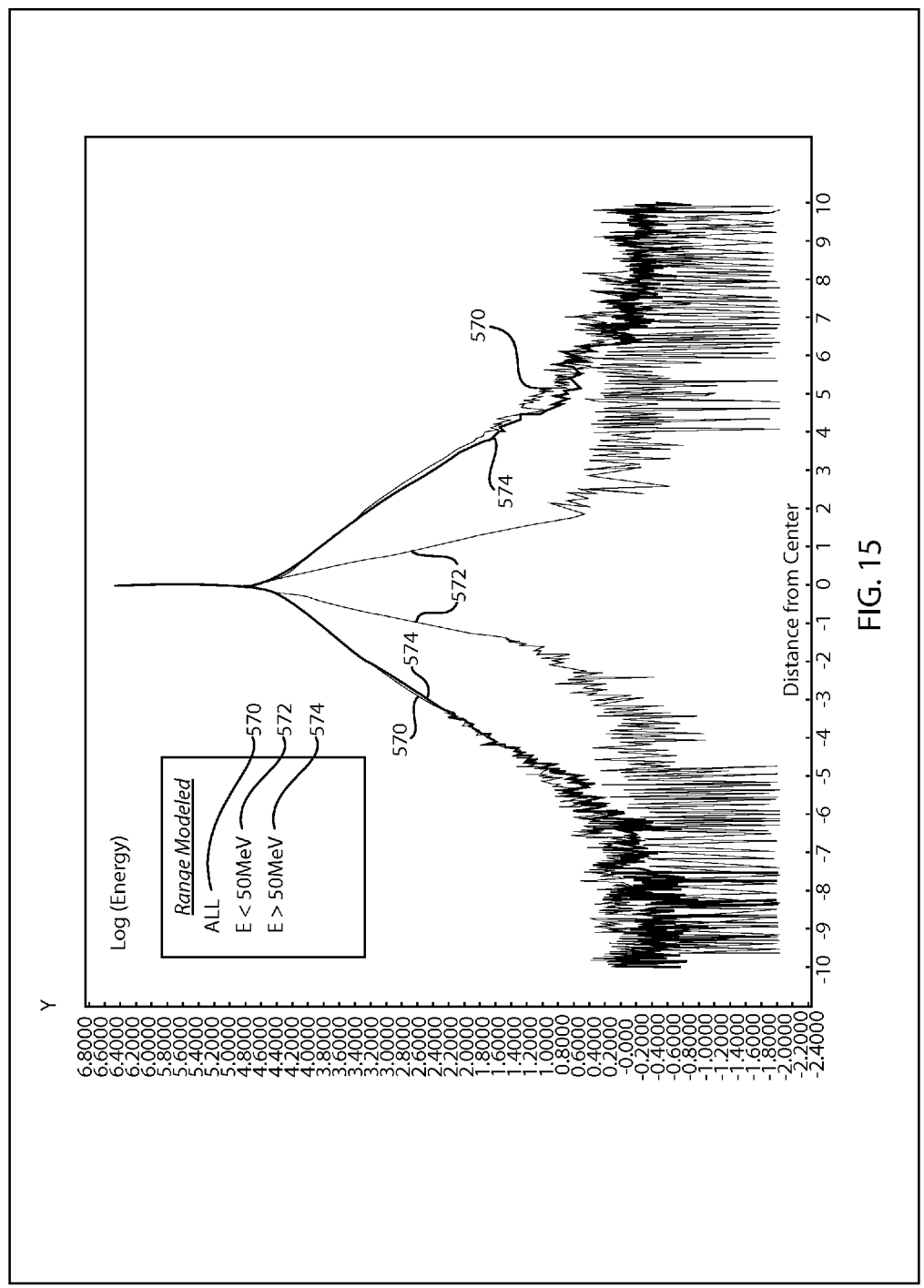
FIG. 15 shows a graph of log(energy) versus distance from center (degrees) for three modeled ranges in accordance with one embodiment.

Referring to FIG. 15, a graph of log(energy) versus distance from center (degrees) shows three modeled ranges. One range 570 shows all energies, one range 572 shows energies less than 50 MeV, and one range 574 shows energies greater than 50 MeV. This graph shows that higher energy models need greater accuracy due to the greater scatter in the range curves. Using modeled data and distributions, means and standard deviations of log(phi) versus log(energy) can be plotted, and a curve can be fit to model the means and standard deviations of an energy (or log (energy)) distribution for a particular material. In one instance, for water a mean=−2.599−22.265 log(energy) was determined with a constant standard deviation of about −0.6. So knowing the energy can provide an accurate estimate of a phi distribution. The comparison of angle models as between the reduced model and the full model shows accurate results can be obtained using the reduced model over a wide range of energies.

The reduced model may need to be tweaked over particular ranges of angles or energies. This can result in a mixture of distributions or conditions that may be stored in a lookup table or programmed into code. The probability and cumulative distribution functions, e.g., $f_1, f_2, \ldots, f_n$ can be tuned. Similar tuning may be employed using other parameters, other models and other functions/distributions as the case may be.

Figure 16:
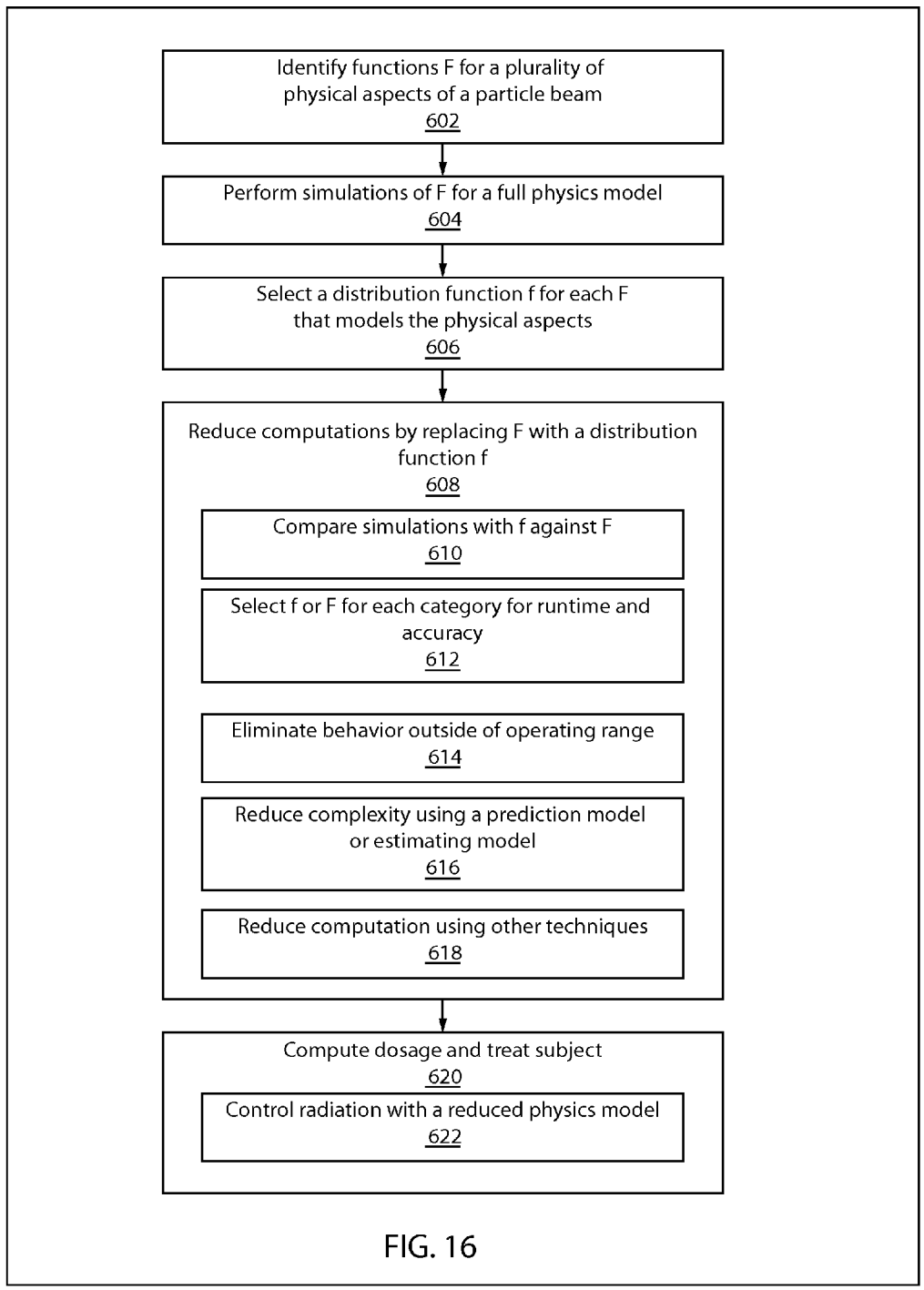
FIG. 16 is a block/flow diagram showing methods for simulating particle beam interactions in accordance with the present principles.

Referring to FIG. 16, methods for simulating particle beam interactions are illustratively described in accordance with the present principles. In block 602, a set of n functions $F_1, F_2, \ldots, F_n$ corresponding to a plurality of different physical aspects of a particle beam are identified. The set of n functions may include, e.g., one or more of particle energy levels, scattering angles, absorption material and/or particle density. Other possible functions may include magnetic field, ion concentration and other beam generating parameters and/or particle interaction parameters. A person skilled in the art may identify other physical aspects for generating or employing a particle beam.

In block 604, simulations of each $F_i$ are performed using a full physics model. In block 606, for each $F_i$, a distribution function $f_i$ is selected that models relevant behavior of the particle beam. The distribution function may include one or more of: probability distribution functions cumulative distribution functions, analytical functions and/or tables. The selection of a distribution function $f_i$ may be based on a computation system being used. For example, a table may be selected over an analytical formula if the processing power is not available. The simulation and optimization module 24 (FIG. 1) may be configured to make such selections in real-time depending on the hardware or software facilities available, e.g., FPGA or GPU versus CPU.

For the example case of modeling energy loss fluctuation, $F_i$ would be a full physics model. An example approach for choosing $f_i$ follows. Discrete energy levels are chosen and full-physics-model-based energy loss fluctuation data is characterized at each energy level. For each energy level, a hybrid approach can be used that models part of the fluctuation distribution using an analytical function, such as a Gaussian, models part of the distribution using discrete bins, potentially representing a pdf or cdf and models part of the distribution using a tail model, such as a generalized pareto model.

Just one of the types of models can also be employed. Boundaries dividing the distribution into parts that are modeled each way are dependent upon the energy level and can be described as an analytical function of energy or in a table. Parameters of analytical models are also dependent upon the energy level and similarly also can be described as analytical functions of energy or in a table. Boundaries can be chosen to trade-off accuracy versus computation ease and may vary based on the goal of the simulation (e.g., faster/less accurate versus lower/more accurate) and based on the computation hardware/software being used (e.g., CPU versus GPU).

The set of simulations used to determine accuracy can include comparing reduced results to full-physics results on the dose distribution in a water phantom, as illustrated here, but also may include comparing efficacy of treatment plans using metrics important to a treatment plan, namely the amount of dose accumulated in the target (tumor) and in regions to avoid (organs-at-risk). Generally a high dose is desired in the former and a low dose in the later.

In block 608, computations of the full physics model, corresponding to each $F_i$, are reduced by replacing $F_i$ with the distribution function $f_i$. In block 610, reducing computations includes comparing a set of simulations wherein each $f_i$ replaces its respective $F_i$ to determine if relevant behavior is accurately modeled. In block 612, reducing computations includes selecting one of $f_i$ or $F_i$ for each n, for a Monte Carlo simulation based on a runtime and accuracy criteria. In block 614, reducing computations may include eliminating distributions outside of an operating range. In block 616, reducing computations may include reducing complexity by generating a prediction model or an estimating model that maintains accuracy. In block 618, computations may be reduced using other techniques.

In block 620, particle dosage is computed using at least one $f_i$ to reduce computation time. In block 622, the dosage may be employed to treat a lesion. The dosage may include protons, although other forms of radiation are contemplated. The radiation source is controlled in accordance with a reduced physics model including at least one $f_i$.

Hardware Acceleration: the use of hardware accelerators such as graphics processing units (GPUs), FPGAs and multi-core processors can be provided to further enhance accelerated computation times. GPUs-as-accelerators for compute-intensive work other than graphic processing (GPGPUs or General-purpose GPUs) consist of hundreds to thousands of small cores designed for parallel computation. Computationally-intensive parallel workloads can achieve high performance utilizing a commodity PC by taking advantage of the GPU's high floating-point throughput and memory bandwidth.

The Open Computing Language (OpenCL) is a framework that enables programmers to access various accelerators in a C-based unified way without proprietary graphics programming techniques sometimes used in GPU programming or writing lower-level HDL (hardware description language) constructs for FPGAs.

Platforms and Hardware: We initially experimented with JACK in two multi-core systems, both as a single-threaded and parallel application utilizing the pthreads library. The first system included an Intel Core i7-920 CPU running at 2.66 GHz with an 8 MB L2 cache and 6 GB of main memory. There are 4 cores, each with 2 hardware contexts for a total of 8 hardware threads. This same system was then used to run JACK using the pthread library with 2, 4 and 8 threads. For greater pthread scalability tests, we ran the parallel JACK on an IBM POWER P730™ box with 2 POWER7 chips running at 3.875 GHz with 48 GB of main memory. Each chip has 8 cores, and each core has 4 independent hardware threads for a total of 64 independent hardware contexts.

To explore the speedups possible via GPU execution, we experimented with the OpenCL JACK version of the code on a system comprised of an Intel Core 2 Quad CPU running at 2.66 GHz with a 4 MB cache and 4 GB of DRAM. This system also contained an NVIDIA™ GeForce™ GTX 295 GPU card with 240 GPU cores running at 1.24 GHz and a total of 896 MB of memory. Other GPU devices may also be employed that may provide greater performance.

Implementation: For JACK with OpenCL, a CPU works as the host and is responsible for the initialization process, which then transfers the data into OpenCL kernels. These OpenCL kernels are then run on the CPU or GPU and execute the Monte Carlo proton algorithms described above. To reduce average memory access latency, all possible structures (e.g., the current state of a proton) and variables are moved into local or private memory due to the long latencies associated with access global memory in the GPU. Since there is no built-in random number generator function in OpenCL, we provide one in the JACK code. This functionality also runs in an OpenCL kernel to generate random numbers and normal distribution values. The initial random seeds are generated by the host CPU and then transferred into the appropriate kernel for each particle. Math functions with the native prefix are invoked in the kernel if available for performance reasons.

Data transfer between the host and device memory can frequently be a bottleneck in GPU computation. As a result, we minimize data transfer as much as possible. The record of the particle's individual steps (constituting a "track") tests the limits of memory capacity, necessitating particles to be divided into "batches" to prevent running out of resources. For example, over 500 MB is needed for the tracking records for a quarter of a million particles. We can divide the job into four batches for one million protons to avoid memory access related problems.

Results: experimental results for 10,000 and 1,000,000 protons were obtained, and we varied certain parameters in JACK that have a high impact on overall performance. The step size, for example, has an almost linear effect on run time. By default, we chose a step size of 0.01 mm to achieve suitably accurate results. Using higher step sizes will change the resulting distribution and may result in degradation in the accuracy of the results. The voxel size of our geometry was found not to be a large factor in performance, even though we split our data collectors among threads and then perform a reduction at the end of a run. Also, the kinetic energy has a non-linear scaling effect on the performance of the JACK code. To put the results into perspective, a single-threaded run of GEANT4™ (only Electromagnetic Interactions for a proper comparison) for 1,000,000 protons with a step size of 0.01 mm takes on the order of 38 hours to complete on an i7, resulting in a maximum 3446× speedup for JACK across all architectures mentioned here.

Multi-threaded (pthread) Results: speedup results when utilizing pthreads on the i7 for up to 8 threads was performed. A maximum speedup of 5.2 is achieved when using all 8 hardware thread contexts. Note that speedup is linear through 4 threads, after which time threads are forced to share some CPU resources (due to the hyperthreaded architecture of the Intel i7 core) and resulting in worsening parallel efficiency. Similarly, the P730 results scale linearly up to 32 threads, and then efficiency begins to fall off as the 4 threads compete for some CPU resources such as a shared pipeline, floating point units, etc. The 16-core Power P730™ achieves a nearly 40× performance improvement over the initial JACK implementation for a 1M particle-sized problem.

Scaling with Problem Size: the performance of the multi-threaded version of JACK on 8 threads for two different step sizes and three different problem sizes shows that as the number of particles increases, the scalability of the application improves because there is more work available for each thread, reducing fixed-cost overhead of the final synchronization and reduction operations. At smaller problem sizes, smaller step sizes also serve to provide more work for each thread, improving scalability as shown by the 0.01 mm versus 0.1 mm bars.

Core 2 OpenCL versus GPU OpenCL: Although the maximum frequency of the GPU is less than half that of the host Core 2 CPU, the massive parallelism available by using the GPU enables a 10-fold performance improvement when running the OpenCL code on both processing elements with a large number of protons. Because the simulation is parallel, JACK is very amenable to the type of parallelism offered by GPU systems. There are 30 compute units in the NVIDIA™ GTX 295™ per core, and 8 streaming processors per compute unit for a total of 240 streaming processors in a single core of an NVIDIA™ GTX295™. For the INTEL™ Core 2 CPU, there are a total of 4 compute units running at twice the frequency of the GPU units. The GPU is able to support thousands of active threads per multiprocessor, and it is well suited for running large-scale and highly parallelizable code such as Jack.

GPU: With a million incident particles, the NVIDIA™ GPU achieves a speedup of around 64× that of the single threaded JACK. The larger the number of particles, the more parallelizable work can be distributed to the streaming processors of the GPU adding both improved performance and improved accuracy. This effect is demonstrated over various step and problem sizes on the GPU. Tolerating memory latency is achieved via utilizing a high degree of multithreading, e.g., warps in the GPU. A warp is a group of threads executed together to take advantage of data processed in a SIMD (single-instruction multiple-data) fashion by the GPU. When one warp stalls due to a memory access, processors choose another ready warp to work on. Switching the workload from stalled warps to ready warps repeatedly keeps the streaming processors busy and parallel efficiency high.

MCNPX is a general-purpose Monte Carlo radiation transport code for modeling the interaction of radiation with matter. MCNPX stands for Monte Carlo N-Particle eXtended. It extends the capabilities of MCNP4C3 to nearly all particles, nearly all energies, and to nearly all applications without an additional computational time penalty. MCNPX is fully three-dimensional and time dependent. It utilizes the latest nuclear cross section libraries and uses physics models for particle types and energies where tabular data are not available. Applications range from outer space (the discovery of water on Mars) to deep underground (where radiation is used to search for oil.)

MCNPX is used for nuclear medicine, nuclear safeguards, accelerator applications, homeland security, nuclear criticality, and much more. MCNPX is written in Fortran 90, runs on PC Windows, Linux, and Unix platforms, and is fully parallel (PVM and MPI). MCNPX still suffers from too much overhead from a large framework designed to apply to most situations as opposed to the focus on proton therapy.

FDC: The Fast Dose Calculator (FDC) is a Monte Carlo track-repeating algorithm based on GEANT4™. FDC was developed to increase computation speed without diminishing dosimetric accuracy. The algorithm used a database of proton trajectories in water to calculate the dose of protons in heterogeneous media. The extrapolation from water to 41 materials was achieved by scaling the proton range and the scattering angles. The scaling parameters were obtained by comparing GEANT4™ dose distributions with those calculated with FDC for homogeneous phantoms.

The FDC algorithm was tested by comparing dose distributions in a voxelized prostate cancer patient as CPU time required for a complete dose calculation in a voxelized patient anatomy by more than two orders of magnitude, while on average reproducing the results from the Monte Carlo predictions within 2% in terms of dose and within 1 mm in terms of distance. Since it is not a true Monte Carlo based simulation, it cannot guarantee the same usability and control over modeling.

SMC: The National Cancer Center hospital in Japan has implemented a simplified Monte Carlo (SMC). Though it has relatively good accuracy, speed and has a home-grown philosophy that is close to ours, the SMC could modify some models for more accuracy. It uses the Highland formula for multiple Coulomb scattering which has been shown to have issues in the tails in addition to ignoring absorption and lateral scattering due to nuclear reactions. JACK™ is usable for both clinical and research applications in medical physics and so the proper incorporation and ability to separate different models from each other is important.

In accordance with the present principles, a fast and accurate in-house Monte Carlo simulation for proton therapy called JACK has been implemented. It has been able to achieve on the order of 3446× speedup over GEANT4™, and using a Power P730 box, a 2104× speedup is achieved, which easily beats GEANT4™. With hardware acceleration on GPUs, we easily get >3000× speedup over GEANT™.

Having described preferred embodiments of fast and accurate proton therapy dose calculations (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for simulating particle beam interactions for reducing computation time of particle dosage applied to a lesion, comprising:
    identifying a set of n functions $F_1, F_2, \ldots, F_n$ corresponding to a plurality of different physical aspects of a particle beam;
    performing simulations of each $F_i$ using a full physics model;
    selecting for each F a distribution function $f_i$ that models relevant behavior of the particle beam;
    reducing computation of the full physics model corresponding to each $F_i$ by replacing $F_i$ with the distribution function $f_i$, wherein reducing computation includes:
    computing the particle dosage using at least one f;
    computing energy loss fluctuations in the particle beam;
    comparing a set of simulations wherein each $f_i$ replaces Its respective $F_i$ to determine if relevant behavior is accurately modeled; and
    selecting one of $f_i$ or $F_i$ for each n, for a Monte Carlo simulation based on a runtime and accuracy criteria;
    treating the lesion based on the computed particle dosage and the computed energy loss fluctuations.

2. The method as recited in claim 1, wherein the set of n functions includes one or more of particle energy levels, scattering angles, absorption material or particle density.

3. The method as recited in claim 1, wherein the particle beam includes protons.

4. The method as recited in claim 3, wherein the energy loss fluctuations are based on multipliers of cumulative distribution functions.

5. The method as recited in claim 1, wherein reducing computation includes eliminating distributions outside of an operating range.

6. The method as recited in claim 1, wherein reducing computations includes reducing complexity by generating a prediction model or an estimating model that maintains accuracy.

7. The method as recited in claim 1, wherein the distribution function includes one or more of probability distribution functions and/or cumulative distribution functions.

8. The method as recited in claim 1, wherein the distribution function $f_i$ includes one or more of an analytical function or table.

9. The method as recited in claim 1, wherein selecting for each $F_i$ a distribution function $f_i$ includes selecting $f_i$ based on a computation system being used.

10. The method as recited in claim 1, further comprising controlling a radiation source in accordance with a reduced physics model including at least one $f_i$.

11. A non-transitory computer readable storage medium comprising a computer readable program for simulating particle beam interactions for reducing computation time of particle dosage applied to a lesion, wherein the computer readable program when executed on a computer causes the computer to perform steps of:
    identifying a set of n functions $F_i, F_2, \ldots, F_n$ corresponding to a plurality of different physical aspects of a particle beam;
    performing simulations of each $F_i$ using a full physics model;
    selecting for each $F_i$ a distribution function f that models relevant behavior of the particle beam;
    reducing computation of the full physics model corresponding to each $F_i$ by replacing $F_i$ with the distribution function $f_i$, wherein reducing computation includes:
    computing the particle dosage using at least one $f_i$;
    computing energy loss fluctuations in the particle beam; and
    comparing a set of simulations wherein each $f_i$ replaces its respective $F_i$ to determine if relevant behavior is accurately modeled; and
    selecting one of $f_i$ or $F_i$ for each n, for a Monte Carlo simulation based on a runtime and accuracy criteria; and
    treating the lesion based on the computed particle dosage and the computed energy loss fluctuations.

12. The non-transitory computer readable storage medium as recited in claim 11, wherein the set of n functions includes one or more of particle energy levels, scattering angles, absorption material or particle density.

13. The non-transitory computer readable storage medium as recited in claim 11, wherein the particle beam includes protons.

14. The non-transitory computer readable storage medium as recited in claim 13, wherein the energy loss fluctuations are based on multipliers of cumulative distribution functions.

15. The non-transitory computer readable storage medium as recited in claim 11, wherein reducing computation includes eliminating distributions outside of an operating range.

16. The non-transitory computer readable storage medium as recited in claim 11, wherein reducing computations includes reducing complexity by generating a prediction model or an estimating model that maintains accuracy.

17. The non-transitory computer readable storage medium as recited in claim 11, wherein the distribution function includes one or more of probability distribution functions and/or cumulative distribution functions.

18. The non-transitory computer readable storage medium as recited in claim 11, wherein the distribution function $f_i$ includes one or more of an analytical function or table.

19. The non-transitory computer readable storage medium as recited in claim 11, wherein selecting for each $F_i$ a distribution function $f_i$ includes selecting $f_i$ based on a computation system being used.

20. The non-transitory computer readable storage medium as recited in claim 11, further comprising controlling a radiation source in accordance with a reduced physics model including at least one $f_i$.

21. A system for simulating particle beam interactions for reducing computation time of therapy-doses particle dosage applied to a lesion, comprising:
   a dose computation module configured in non-transitory stored media to reduce computation of a full physics model corresponding to a set of n functions $F_1$, $F_2, \ldots, F_n$ for a plurality of different physical aspects of a particle beam, wherein at least one $F_i$ is replaced with a distribution function $f_i$ to reduce computation by computing the particle dosage using, at least one $f_i$ by computing energy loss fluctuations in the particle beam, where $f_i$ models relevant behavior of the particle beam;
   a simulation and optimization module configured to compare a set of simulations wherein each $f_i$ replaces its respective $F_i$ to determine if relevant behavior is accurately modeled and to selecting one of $f_i$ or $F_i$ for each n, for a Monte Carlo simulation based on a runtime and accuracy criteria; and
   treat the lesion based on the computed particle dosage and the computed energy loss fluctuations from the dose computation module.

22. The system as recited in claim 21, wherein the set of n functions includes one or more of particle energy levels, scattering angles, absorption material or particle density.

23. The system as recited in claim 21, wherein the particle beam includes protons.

24. The system as recited in claim 21, wherein the energy loss fluctuations are based on multipliers of cumulative distribution functions.

25. The system as recited in claim 21, wherein the simulation and optimization module selects $f_i$ based on a computation system being used.

* * * * *